United States Patent [19]

Mimura et al.

[11] Patent Number: 5,071,955
[45] Date of Patent: Dec. 10, 1991

[54] OCTOPEPTIDE EXHIBITING ANTIMYPERTENSIVE ACTIVITY

[75] Inventors: Tsutomu Mimura; Yasuhiro Kohama, both of Suita; Mikio Satake, Hachioji; Yasukazu Nagase, Tokyo, all of Japan

[73] Assignees: Nippon Suisan Kaisha, Ltd.; Mochida Pharmaceutical Co., Ltd., both of Tokyo, Japan

[21] Appl. No.: 363,772

[22] Filed: Jun. 9, 1989

[30] Foreign Application Priority Data

Jun. 10, 1988 [JP] Japan .................................. 63-143258

[51] Int. Cl.$^5$ ............................ C07K 7/06; C07K 7/14
[52] U.S. Cl. ................................................... 530/328
[58] Field of Search ............................ 530/328; 514/16

[56] References Cited

PUBLICATIONS

Kohama, Y., et al., Biochem. Biophys. Res. Commun., 155(1): 332–337, Aug. 1988.

Stewart, J., et al., Solid Phase Peptide Synthesis, Pierce Chemical Co., 1984.

Kemp, D., et al., Organic Chemistry, Worth Publishers, Inc., 1980.

Kohama, Y., et al., Biochem. Biophys. Res. Commun., 161(2): 456–460, Jun. 1989.

Primary Examiner—Howard E. Schain
Assistant Examiner—Susan M. Perkins
Attorney, Agent, or Firm—Oblon, Spivak, McClelland, Maier & Neustadt

[57] ABSTRACT

A novel peptide possessing excellent antihypertensive activity is disclosed. The peptide has the formula:

Pro-Thr-His-Ile-Lys-Trp-Gly-Asp  (I)

and can be prepared by purifying a fluid extracted from fish tissues or by combining constituting amino acids by a peptide synthesis method. It exhibits excellent ACE inhibitory activity, low toxicity, and good stability, and is thus an extremely useful and effective antihypertensive substance.

5 Claims, 4 Drawing Sheets

OCTOPEPTIDE EXHIBITING ANTIMYPERTENSIVE ACTIVITY

BACKGROUND OF THE INVENTION

1. Field of the Invention

The present invention relates to a novel peptide possessing excellent antihypertensive activity and useful as a pharmaceutical. The invention also relates to a process for the preparation as well as the use of such a peptide.

2. Description of the Background

Various active ingredients have been extracted and collected from the fish tissues. Although some of them have been put into practical use as pharmaceuticals and the like, it is believed that more physiologically active substances should be obtainable. This invention was achieved based on such contemplation.

The present inventors have conducted research over a long period of time about the components of fish tissues, and found that a certain component extracted and isolated from fish tissues possessed a strong antihypertensive action. The inventors have undertaken investigations to identify such an active component and found that the component was a peptide represented by the following formula (I), Pro-Thr-His-Ile-Lys-Trp-Gly-Asp    (I)

SUMMARY OF THE INVENTION

Accordingly, an object of the present invention is to provide a peptide represented by the following formula (I), Pro-Thr-His-Ile-Lys-Trp-Gly-Asp    (I)

[Such a peptide is hereinafter referred to as Peptide (I)]

As a preferred embodiment, the present invention provides Peptide (I) which is prepared by purifying an extract from fish tissues.

As another preferred embodiment, the present invention provides Peptide (I) which is prepared by combining constituting amino acids by a peptide synthesis method.

Another object of the present invention is to provide a process for preparing Peptide (I).

Still another object of the present invention is to provide an antihypertensive agent which comprises as an active ingredient Peptide (I).

Other objects, features and advantages of the invention will hereinafter become more readily apparent from the following description.

DETAILED DESCRIPTION OF THE INVENTION AND PREFERRED EMBODIMENTS

Figure 1:
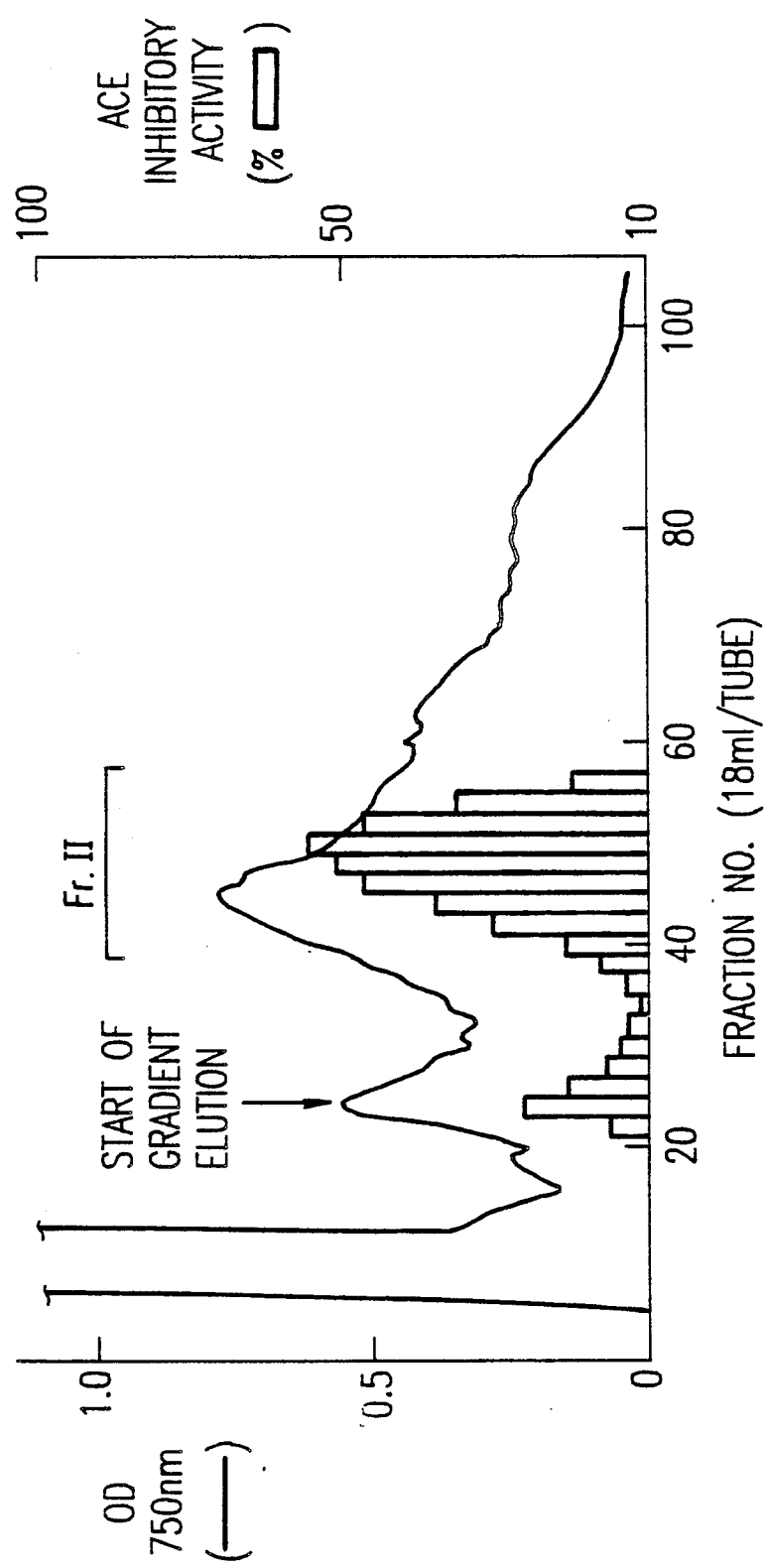
FIG. 1 is an elution pattern obtained when Fr. I (hereinafter defined) was purified using SP-Sephadex C-25.

The peptide of the present invention can be extracted, for example, from fish tissues according to the following methods.

Fish tissue is added to an aqueous solution of acetic acid-HCl, heated for several minutes up to several tens of minutes at 100°–150° C., and then extracted. This extracted fluid is adsorbed to a resin such as octadecyl silica gel (ODS) and then the fraction eluted with acetonitrile is collected (such a fraction is herein abbreviated as "Fr. I"). The Fr. I is further refined chromatographies on a SP-Sephadex C-25 and Sephadex G-25 column. The peptide of formula (I) is separated using high performance liquid chromatography (HPLC).

Fish which can be used include the Thunus (tuna), Scomber (mackerel), Sadinops (sardines), Cololabis (saury), Lateolabrax (sea bass), Clupea (herring), Trachurus (horse mackerel), Paralichths (flounder), Suggrundus (flat head), Doryteuthis (squid), Limanda (marbled sole), Sphyraene (barracuda), Trichiurus (cutlass fish), Ocycrius (Japanese butterfish), Anoplopoma (beshow), Pampus (harvest fish), and the like.

Fish tissues from which the peptide having the amino acid sequence of formula (I) can be extracted include, for example, white muscle, heart, dark muscle, liver, testis, ovary, and the like. White muscle is the most desirable because it contains a lot of Peptide (I) and is readily available in large quantities.

The peptide of the present invention can also be prepared by conventional peptide synthesis methods.

Liquid phase methods and solid phase methods can both be used as peptide synthesis methods. Commercially available peptide synthesizing apparatus may be used for the synthesis. Peptide of formula (I) can be purified and isolated by reverse-phase column chromatography used in conventional peptide separation.

The antihypertensive action of the peptide of the present invention was measured as Angiotensin I converting enzyme (ACE) inhibitory activity according to the method of Cushman and Cheung [Biochem. Pharmacol., 20, 1637 (1971)].

A prescribed amount of sample was added to a solution composed of 1–10 mU ACE, 2.5 mM Hip-His-Leu substrate (produced by Peptide Research Institute), 100 mM potassium-phosphate buffer (pH 8.3), and 300 mM NaCl. 0.25 ml of this mixture was incubated at 37° C. for 30 min, and the enzymatic reaction was stopped by adding 0.25 ml of 1N HCl. 1.5 ml of ethylacetate was then added and the mixture was vigorously shaken for 10 second, following which the hippuric acid produced was extracted. A 1 ml aliquot of the extract was evaporated to dryness and the residue was dissolved in 1 ml of distilled water to measure the hippuric acid concentration from the absorbance at 228 nm (ODs). A blank (ODsbl) was made by adding 1N HCl prior to incubation, and the difference in absorbance, ODs-ODsbl, was determined. A control (ODc) to which no sample had been added was prepared and the difference ODc-ODcbl was determined in the same way. ACE inhibitory activity was calculated using the following equation:

$$ACE \text{ inhibitory activity } (\%) = \left(1 - \frac{OD_s - OD_{sbl}}{OD_c - OD_{cbl}}\right) \times 100$$

Table 1 shows comparison of ACE inhibitory activities of the peptide of the present invention [Peptide (I)], a porcine plasma tripeptide (Leu-Val-Leu), an 11 peptide viper toxin (Pyr-Gly-Pro-Pro-Pro-Arg-Pro-Lys-Ile-Pro-Pro), and the synthetic pharmaceutical Captopril.

TABLE 1

| Sample | Origin | M.W. | ACE Inhibitory Activity $IC_{50}$ ($\mu$M) |
|---|---|---|---|
| Peptide (I) | Fish | 952 | 0.7 |
| Peptide (I) | Peptide Synthesis | 952 | 0.6 |
| Tripeptide | Porcine plasma | 343 | 1.7 |
| 11 Peptide | Viper Toxin | 1,052 | 1.5 |
| Captopril | Chemical Synthesis | 217 | 0.08 |

The peptide of formula (I) of the present invention, irrespective of its source, showed excellent ACE inhibitory activity indicating that it is useful as an antihypertensive agent.

Intravenous and oral administration are desirable as means of administration.

Preparation forms which can be used include injections, and oral administration formulations such as capsules, tablets, powder preparations, granules, and the like.

Normal daily therapeutic dose of Peptide (I) in adults is 0.1–1,000 mg, although an optimum dose will differ depending on the conditions of the patient, the means of administration, and the like.

Peptide (I) can be made into pharmaceutical preparations together with conventional pharmaceutical components such as carriers, bases, and excipients according to commonly available methods. For oral administration preparations it is desirable to use them as oil-soluble capsules, tablets, powders, or granules, while for injections water-soluble injection preparations or freeze-dried powder preparations are preferable. Although it is possible to use conventional substances as excipients, the use of human serum albumin, sucrose, gelatin, starch, polyethylene glycol, or the like are preferable.

Other features of the invention will become apparent in the course of the following description of the exemplary embodiments which are given for illustration of the invention and are not intended to be limiting thereof.

EXAMPLES

EXAMPLE 1

(i) Two (2) kg of white muscle of *Neothunnus macropterus* (Pacific yellow-finned tuna) minced and homogenized with 8 volumes of cold 1M acetic acid—20 mM HCl. The suspension was autoclaved at 120° C. for 5 minutes, cooled and centrifuged at 16,000 rpm for 20 minutes. 80 g of activated ODS resin (55–105 $\mu$M) was added to the supernatant and stirred for 1 hour. The ODS recovered by filtration on a glass filter was washed with 800 ml of 4% acetic acid and eluted with 1 liter of 15% acetonitrile. The 15% acetonitrile fraction was evaporated under reduced pressure and 1,060 mg of Fr. I was obtained. The $IC_{50}$ value for the AEC of this fraction was 530 $\mu$M.

(ii) Fr. I was dissolved in 0.2M acetic acid and absorbed on a SP-Sephadex C-25 column (1.8×50 cm). The column was washed with 0.2M pyridine-acetate, pH 3.1 and then developed with 0.2M pyridine-acetate, pH 3.1, −2.0M pyridine-acetate, pH 5.0. The elution pattern is shown in FIG. 1. The ACE inhibitory activity emerged in Fr. II. The $IC_{50}$ value for the ACE of this fraction was 188 $\mu$M.

Figure 2:
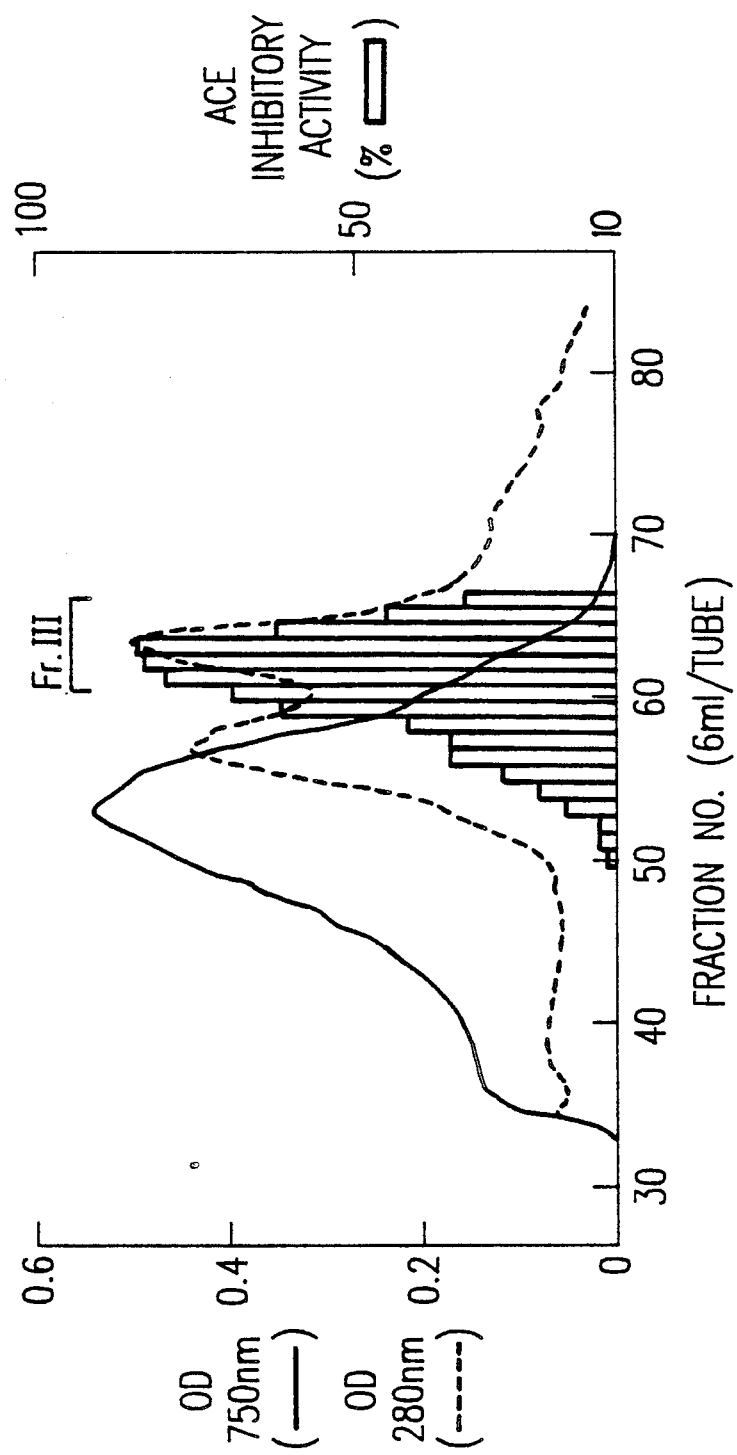
FIG. 2 shows a similar elution pattern obtained when Fr. II (hereinafter defined) was purified using Sephadex G-25 column.

(iii) Fr. II was passed through a column (2.5×93 cm) packed with Sephadex G-25 and eluted with 0.2M acetic acid. The elution pattern is shown in FIG. 2. The fraction exhibiting ACE inhibitory activity was collected as Fr. III. The $IC_{50}$ value for the ACE of this fraction was 100 $\mu$M.

Figure 3:
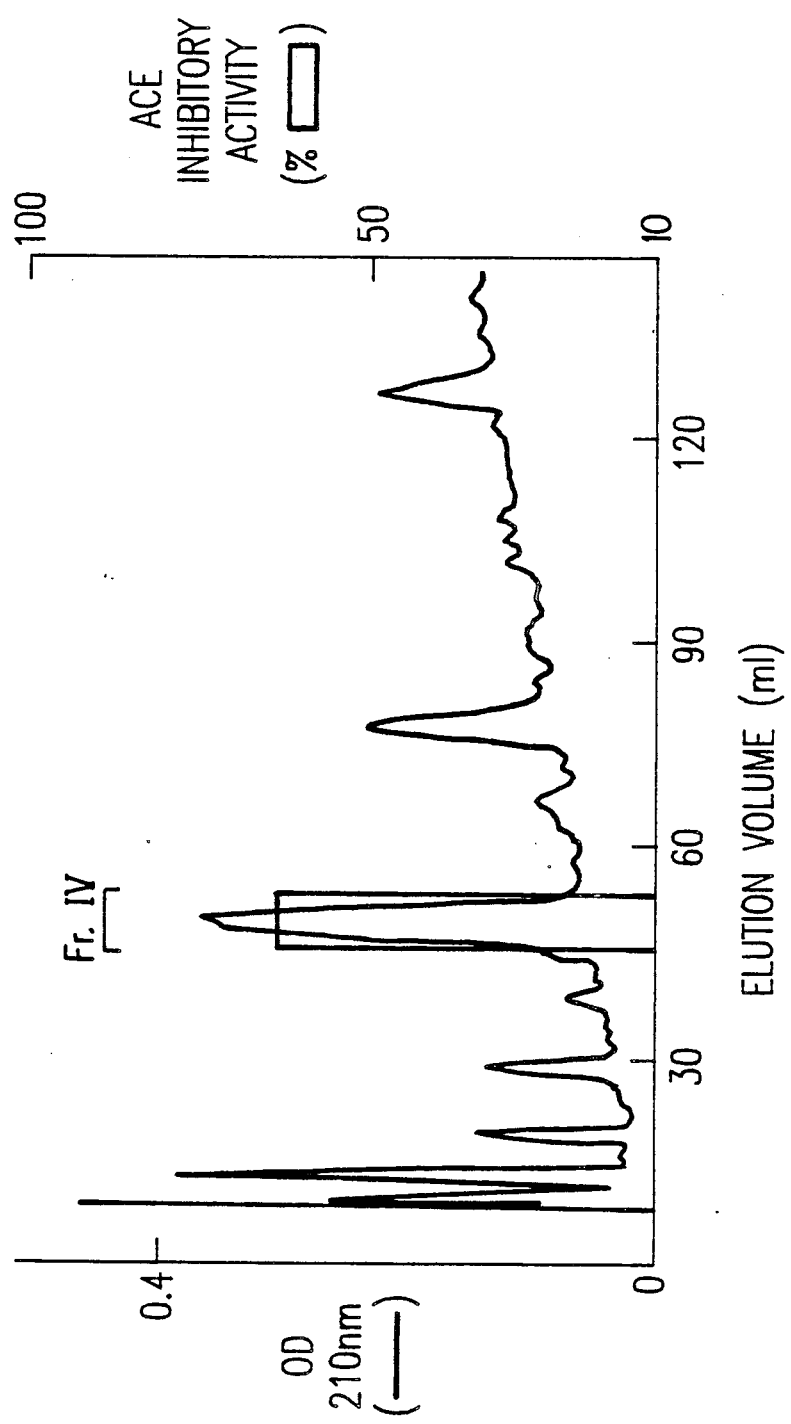
FIG. 3 is an elution pattern obtained when Fr. III (hereinafter defined) was run on an HPLC system using Develosil ODS-7.

(iv) Fr. III was subjected to HPLC on a Deverosil ODS-7 column (0.8×25 cm, eluate: 10–20% $CH_3CN$ in 0.05% HCl). The elution pattern is shown in FIG. 3. The ACE inhibitory activity recovered in this fraction (Fr. IV) was 50 $\mu$M.

Figure 4:
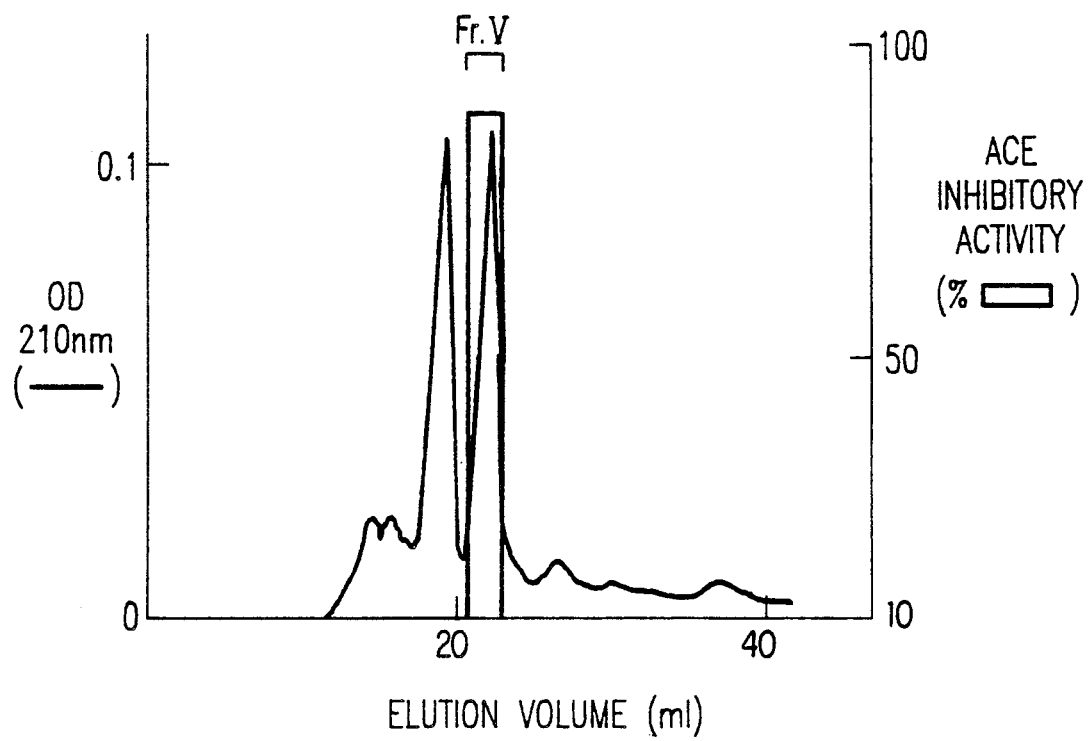
FIG. 4 presents an elution pattern obtained when Fr. IV (hereinafter defined) was run on an HPLC using Asahipak GS-220.

(v) Fr. IV was subjected to HPLC on an Asahipak GS-220 column (0.76×50 cm, eluant: 50 mM sodium phosphate buffer, pH 7.0). The elution pattern is presented in FIG. 4. The ACE inhibitory activity was recovered in a symmetrical peak (Fr. V). Finally, rechromatography by reverse-phase HPLC was necessary for desalting. The solvent was evaporated under reduced pressure and 0.8 mg of the octapeptide of the present invention was obtained.

Amino acid composition:

Hydrolysis was carried out for 20 hours at 110° C. in 6N HCl or 4M methane sulfonic acid. The results obtained using the Pico-TAG amino acid analytical method are presented in Table 2.

TABLE 2

|  | 6 N HCl | 4 M methane sulfonic acid |
|---|---|---|
| Asp | 1.1 (1) | 1.1 (1) |
| Gly | 1.1 (1) | 1.2 (1) |
| His | 1.0 (1) | 1.0 (1) |
| Thr | 1.0 (1) | 0.9 (1) |
| Pro | 1.0 (1) | 1.1 (1) |
| Ile | 1.0 (1) | 1.0 (1) |
| Trp |  | 0.8 (1) |
| Lys | 0.9 (1) | 0.9 (1) |

Amino acid sequence:

The amino acid sequence determined using a gas phase protein sequencer (Model 470A, made by Applied Biosystems Co. Ltd.) is shown in Formula (I)

Pro-Thr-His-Ile-Lys-Trp-Gly-Asp    (I)

C-terminal amino acid analysis:

Asp was determined to be the C-terminal amino acid using the carboxypeptidase method [Biochemical Experiment Lecture 1, Chemistry of Proteins II, p 203]. This result was the same as that found by the gas phase protein sequencer.

Figure 5:
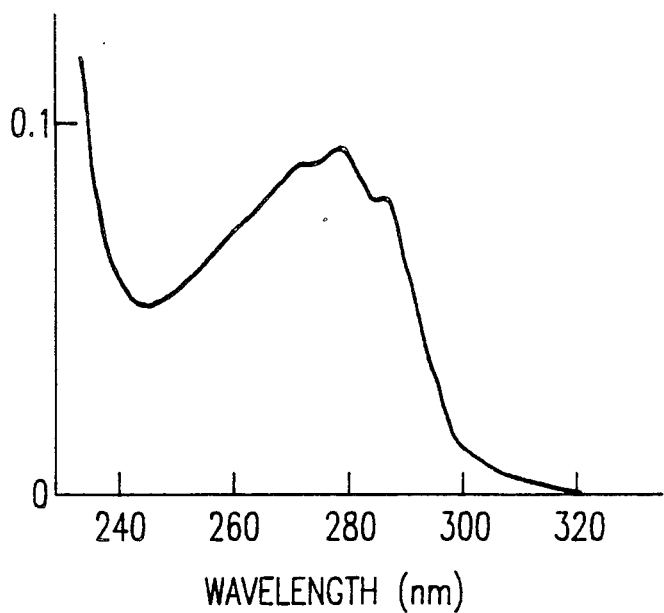
FIG. 5 shows an ultraviolet absorption spectrum of Peptide (I) of the present invention.

Ultraviolet absorption spectrum:

The spectrum is shown in FIG. 5.

EXAMPLE 2

Using a full automatic peptide synthesizer Model 430-A, made by Applied Biosystems Co., Ltd.), the peptide of formula (I) was synthesized.

Pro-Thr-His-Ile-Lys-Trp-Gly-Asp    (I)

Elimination from the resin carrier and protective group removal were carried out using hydrogen fluoride, and then Peptide (I) of the present invention was purified by reversed-phase HPLC using an ODS column.

As in Example 1, the result obtained by measuring the amino acid sequence was in agreement with the value expected from the amino acid sequence of Peptide (I).

EXAMPLE 3

The peptide of formula (I) prepared in Example 2 was dissolved in physiological saline.

Pro-Thr-His-Ile-Lys-Trp-Gly-Asp    (I)

Various concentrations of the peptide in physiological saline were intravenously administered to test animal groups each consisting of 6 week old male (10/group) or female (10/group) ICR mice, or 6 week old male (10/group) or female (10/group) Wistar rats. The $LD_{50}$ value was determined after a 2 week observation period.

The $LD_{50}$ values for Peptide (I) of the present invention in both mice and rats were found to be greater than 10 mg/kg.

As can be seen from the above examples, Peptide (I) of the present invention exhibits excellent ACE inhibitory activity, low toxicity, and safety, indicating that this compound is an extremely useful and effective antihypertensive substance.

Below are further examples explaining specific medical uses of Peptide (I) of the present invention.

EXAMPLE 4

Water-soluble injection preparation 100 mg of peptide of formula (I) prepared in Example 2 was dissolved in 100 ml of 0.01M phosphate buffer (pH 7.0) containing 0.14M NaCl prepared using distilled water for injection use. The solution was filtered aseptically using a membrane filter. Each 1 ml sample of the filtrate was placed in a glass container and the container was tightly sealed to serve it as a water-soluble injection preparation.

EXAMPLE 5

Tablets 1,000 tablets each containing 100 mg of Peptide (I) were prepared from the following components.

| | |
|---|---|
| Peptide (I) prepared in Example 1 | 100.0 g |
| Starch | 50.0 g |
| Gelatin | 7.5 g |
| Crystalline cellulose | 25.0 g |
| Magnesium stearate | 2.5 g |
| Total | 185.0 g |

Peptide (I) and the starch were mixed together with an aqueous gelatin solution. The mixture was dried and pulverized to obtain a fine powder. The crystalline cellulose and magnesium stearate were then mixed with the powder. The resulting mixture was processed by a tablet machine to produce 1,000 tablets each containing 100 mg of the active ingredient.

EXAMPLE 6

Capsules

Capsules were prepared by filling No. 1 gelatin capsules with the mixture consisting of the following components.

| | |
|---|---|
| Peptide (I) | 50 mg |
| Magnesium stearate | 7 mg |
| Lactose | 393 mg |
| Total | 450 mg |

As fully illustrated above, the peptide of formula (I) possesses an excellent ACE inhibitive activity and is useful as an antihypertensive agent.

Obviously, numerous modifications and variations of the present invention are possible in light of the above teachings. It is therefore to be understood that within the scope of the appended claims, the invention may be practiced otherwise than as specifically described herein.

What is claimed is:

1. A purified peptide represented by the following formula (I),

Pro-Thr-His-Ile-Lys-Trp-Gly-Asp    (I)

2. An antihypertensive composition, which comprises:

a pharmaceutically effective amount of a peptide of the formula:

Pro-Thr-His-Ile-Lys-Trp-Gly-Asp    (I)

in combination with a pharmaceutically acceptable excipient.

3. A process for obtaining and purifying a peptide of the formula:

Pro-Thr-His-Ile-Lys-Trp-Gly-Asp which comprises;
extracting fish tissues with an aqueous solution of acetic acid and HCl while it is heated for several minutes up to several hours at 100°–150° C.;
containing the aqueous extract with octadecyl silica gel onto which protein in the fish tissue extract is absorbed;
collecting the desired protein fraction by elution of the resin with acetonitrile;
chromatographically purifying said desired protein fraction on SP-sephadex C-25, thereby obtaining a fraction exhibiting ACE inhibitory activity;
chromatographically purifying said fraction exhibiting ACE inhibitory activity over Sephadex G-25 resin, thereby obtaining a fraction exhibiting enhanced ACE inhibitory activity;
chromatographically purifying said ACE inhibitory activity fraction of enhanced activity on Deverocil ODS-7 thereby obtaining a protein fraction of increased ACE inhibitory activity; and
further chromatographically purifying said fraction of increase ACE inhibitory activity on Asahipak GS-220, thereby obtaining a product protein exhibiting substantial ACE inhibitory activity.

4. The process of claim 3, wherein said fish tissue is obtained from tuna, mackerel, sardines, saury, sea bass, herring, horse mackerel, flounder, flathead, squid, marbled sole, barracuda, cutlass fish, Japanese butter fish, beshow or harvest fish.

5. The process of claim 3, wherein said fish tissue is white muscle, heart, dark muscle, liver, testes or ovary tissue.

* * * * *